United States Patent [19]

Biere et al.

[11] Patent Number: 4,801,714
[45] Date of Patent: Jan. 31, 1989

[54] PROCESS FOR THE PREPARATION OF ERGOLINYLTHIOUREAS

[75] Inventors: Helmut Biere; Gregor Haffer, both of Berlin, Fed. Rep. of Germany

[73] Assignee: Schering Aktiengesellschaft, Berlin and Bergkamen, Fed. Rep. of Germany

[21] Appl. No.: 893,911

[22] Filed: Aug. 6, 1986

[30] Foreign Application Priority Data

Aug. 6, 1985 [DE] Fed. Rep. of Germany ....... 3528576

[51] Int. Cl.$^4$ ............................................. C07D 31/48
[52] U.S. Cl. ........................................ 546/67; 546/68
[58] Field of Search ...................... 546/68, 67; 564/17, 564/30

[56] References Cited

U.S. PATENT DOCUMENTS

| 2,958,680 | 11/1960 | Brooks et al. | 564/17 |
| 4,379,790 | 4/1983 | Horowski et al. | 546/68 |
| 4,740,509 | 4/1988 | Sauer et al. | 546/68 |

FOREIGN PATENT DOCUMENTS

| 278853 | 2/1970 | Australia. | |
| 0082808 | 6/1983 | European Pat. Off.. | |
| 0126968 | 12/1984 | European Pat. Off.. | |
| 1119843 | 12/1961 | Fed. Rep. of Germany. | |
| 2035008 | 12/1971 | Fed. Rep. of Germany. | |
| 3413657 | 10/1985 | Fed. Rep. of Germany | 546/68 |
| 3411981 | 10/1985 | Fed. Rep. of Germany | 546/68 |
| 2093452 | 9/1982 | United Kingdom | 514/288 |

OTHER PUBLICATIONS

Hoffman, Helvetica Chimica Acta, 30 pp. 44–51
Riesel et al, CA88-98497g.

Noller, Chemistry of Organic Compounds, 1965, 3rd edition, pp. 349–350.

*Primary Examiner*—Donald G. Daus
*Assistant Examiner*—Cecilia Shen
*Attorney, Agent, or Firm*—Millen & White

[57] ABSTRACT

Ergolinylthioureas derivatives of the general Formula I

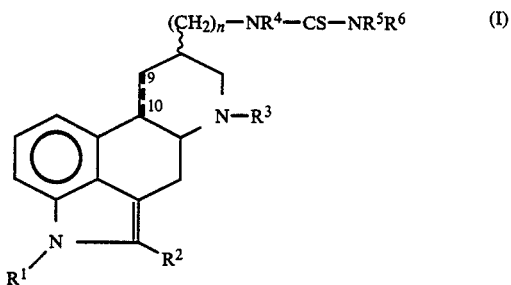

wherein
$R^1$ is hydrogen, lower alkyl or acyl,
$R^2$ is hydrogen, halogen or a lower alkylthio group
$R^3$ is lower alkyl,
$R^4$, $R^5$ and $R^6$, is hydrogen or lower alkyl, and each is identical or different,
n=0, 1 or 2 and $C_9$=$C_{10}$ is a single or a double bond; are produced by reacting in an ergolin-8-ylurea compound otherwise corresponding to Formula I with a —CO—NR$^5$R$^6$ group in place of the —CS—Nr$^5$R$^6$ group is reacted with a chlorinating agent and a thiolating agent.

17 Claims, No Drawings

PROCESS FOR THE PREPARATION OF ERGOLINYLTHIOUREAS

CROSS REFERENCE TO RELATED APPLICATIONS

This application is related to Ser. No. [893727-8-6-86] filed concurrently herewith, whose disclosure is incorporated by reference herewith.

BACKGROUND OF THE INVENTION

This invention relates to a novel process for the preparation of egolinylthioures derivatives by exchange of the carbonyl oxygen of ergolinylthiourea derivatives with sulfur.

The preparation of ergolinylthiourea derivatives has long been known in the art. However, all of the known processes possess severe disadvantages, e.g., they require many synthesis steps and do not produce the desired compounds selectively and in acceptable yields.

For example, processes known heretofore utilize, for the preparation of ergoline thiourea derivatives, 8-aminoergolines which are difficult to obtain. For example, 8-amines of 9,10-didehydroergoline derivatives can be poduced only by way of the multistage Curtius decomposition, yielding an $8\alpha,\beta$-stereoisomer mixture that must be separated with additional work effort, and also resulting in a loss of yield [A. Hofmann, Helv. 30:44 (1947)].

The 8-aminoergoline derivatives with a $C_9$–$C_{10}$ single bond can likewise be prepared only by way of multistage synthesis steps, in poor yields (EP 48 695).

The thus-obtained 8-ergolinylamines have heretofore been reacted either with isothiocyanates or 1,1'-thiocarbonyldiimidazole in order to produce thiourea derivatives.

With the use of isothiocyanates, thiourea derivatives can be obtained in one reaction step. However, this method cannot be used to produce 1,1-dialkyl thioureas which are of particular value in pharmacology.

For the preparation of 1,1-dialkyl thiourea derivatives, 8-ergolinylamines are allowed to react with 1,1'-thiocarbonyldiimidazole and therafter the resultant reactive intermediate product is converted to the desired thiourea derivative with a primary or secondary amine. This preparation method necessitates the use of a highly poisonous, expensive and thus industrially objectionable thiophosgene reagent.

OBJECTS OF THE INVENTION

It is, therefore, an object of the present invention to provide a process for the preparation of ergoline thiourea derivatives which does not possess the aforedescribed disadvantages inherent in the conventional methods, and which makes it possible to produce the ergoline thiourea derivatives in a simple and economical way and in high yields.

Upon further study of the specification and appended claims, further objects and advantages of this invention will become apparent to those skilled in the art.

SUMMARY OF THE INVENTION

These objects are attained by a process for the preparation of ergolinylthiourea derivatives of general Formula I

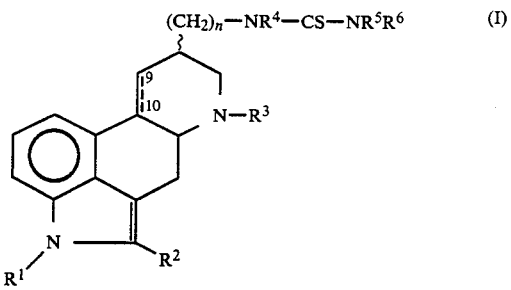

wherein
$R^1$ is hydrogen, lower alkyl or acyl,
$R^2$ is hydrogen, halogen or a lower alkylthio group
$R^3$ is lower alkyl,
$R^4$, $R^5$ and $R^6$, each is hydrogen or lower alkyl, and each is identical or different,
$n=0$, 1 or 2 and $C_9$—$C_{10}$ is a C-C single or a C-C double bond, wherein an ergolin-8-ylurea compound of general Formula II

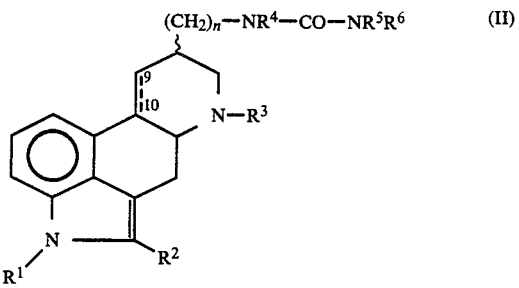

wherein $R^1$, $R^2$, $R^3$, $R^4$, $R^5$, $R^6$ and $C_9$=$C_{10}$ have the values given above, is reacted with a chlorinating agent and a thiolating agent.

DETAILED DISCUSSION

It has been found, in the attainment of these objects, that it is possible to convert the ergoline-8-ylurea derivatives (EP 21 206), which are themselves readily accessible in good yields, under gentle reaction conditions, without a change in configuration and in good yields, into the desired thiourea derivatives with the use of a thiolating agent.

Compounds of Formula II are all conventionally available and are themselves prepared by fully conventional methods well known to those skilled in the art. For the preparation of compounds of Formula II, see, e.g., V. Zikan et al., Coll. Czech. Chem. Comm. 25 (1960) 1922; British Pat. No. 1,174,617; U.S. Pat. Nos. 3,953,454; 4,379,790; European Patent Application No. 56 358 and No. 74921 and U.S. patent application Ser. No. 452,521, filed on Dec. 23, 1982 whose disclosure is incorporated by reference herein.

The process of this invention has the advantages that chlorination of the indole does not occur and the double bonds do not react. Moreover, the process proceeds with complete retention of the desired stereo configuration.

The thiourea derivatives of general Formula I produced according to this invention either are themselves pharmacologically active (See DOS No. 3,240,727 and EP No. 82 808 and the above-identified concurrently filed application) or can be utilized as intermediates for the preparation of valuable medicines. The compounds of Formula I wherein $R_1$=lower alkyl show an especially pronounced central $\alpha_2$-receptor blocking activity, in comparison with the ergoline urea derivatives which are not alkylated in the 1-position. Compounds having such a profile of effectiveness are particularly valuable for the treatment of psychic disturbances of depression related symptoms since, after central $\alpha_2$-receptor blockage, increased release of noradrenalin is effected in the brain, with the consequence of an antidepressant therapeutic effect. Accordingly, the compounds of Formula I wherein $R_1$ is lower alkyl are effective anti-depressants. For example, they can be used to treat endogenous depression, agitated as well as restrained depression and depression without identified specific causes. Typical symptoms which can be relieved include lack or loss of motivation, interest, concentration, hope or energy as well as feelings of emptiness.

As used herein, lower alkyl in Formula I means $C_{1-4}$ alkyl, e.g., methyl, ethyl, n-propyl, isopropyl, n-butyl, sec-butyl, tert-butyl and isobutyl.

Halogen means to.chlorine, bromine or iodine.

The lower alkylthio group preferably contains 1-2 carbon atoms, e.g., the methylthio or ethylthio.

The acyl residue of R1 preferably contains up to 4 carbon atoms and more preferably is derived from a simple carboxylic acid, which preferably is a hydrocarbon acyl acid, e.g., an aliphatic acid, for example, from formic acid, acetic acid, propionic acid or butyric acid.

The substituent in the 8-position can be in the $\alpha$- or $\beta$-position. When $C_9$=$C_{10}$ is a single bond, the hydrogen atom in the 10-position is in the $\alpha$-position.

In the process of this invention, the ergolin-8-ylurea derivative is treated with a chlorinating agent to convert the ergolin-8-ylurea into a reactive ergoline salt. The salt is reacted with a thiolating reagent to produce the corresponding ergolin-8-ylthiourea derivative.

Suitable chlorinating agents including those like phosphorus oxychloride are preferred.

Aggressive chlorinating agents like elemental chlorine are not suitable.

Preferably, the ergolin-8-ylurea derivative is converted with phosphorus oxychloride into a reactive ergoline salt, and the latter is converted to the corresponding ergolin-8-ylthiourea derivatives with a thiolating reagent.

The conversion to the ergoline salt is performed in an inert, preferably aprotic solvent, for example in chlorinated hydrocarbons, such as dichloromethane, dichloroethane; ethers, such as diethyl ether, tetrahydrofuran, dioxane; ketones, such as acetone, methyl ethyl ketone, acetonitrile, etc.

The reaction temperature can vary widely, e.g., from $-50°$ to $+80°$ C.; temperatures of 20° C. to room temperature are preferred. Phosphorus oxychloride is preferably utilized in the reaction in molar excess, e.g., 2-10, preferably 2-4 molar excess.

The thus-obtained activated ergoline urea salts can be isolated with exclusion of moisture or can be reacted with the thiolating agent without isolation.

Suitable thiolating agents are all known thio nucleophiles, such as, for example, alkali xanthates, alkali or alkaline earth sulfides, thiourea, Bunte salts, etc. Alkali metal xanthates, such as potassium ethylxanthate, potassium methylxanthate, and alkali metal sulfides, such as sodium sulfide, potassium sulfide, are preferred.

All inert solvents are suitable for conducting the thiolating reaction, the aforementioned ones as well as dimethylformamide, dimethyl sulfoxide, etc., and also protic solvents, such as alcohols, e.g., ethanol, methanol, propanol, etc.

The reaction mixture can be maintained as a homogeneous mixture as well as a non-homogenous mixture at low temperatures, e.g., from $-30°$ to $+20°$ C., yielding rapidly and completely the desired end products.

In general, the thiolation is effected at $-20$ C. to room temperature, but in special cases it is also possible to work at an elevated temperature, e.g., from $+20°$ to 80° C., for acceleration and completion of the reaction.

The reaction goes to completion in 1-5 hours and is preferably performed under a protective gas atmosphere, such as, for example, under argon or nitrogen.

The reaction product is worked up by means of fully conventional methods, e.g., crystallization or filtration and optionally also by purification with the use of chromatography.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

Preparation of Starting Materials 1,1-Diethyl-3-(1,6-di-n-propyl-8$\alpha$-ergolinyl) urea Under nitrogen, 2 g of 1,1-diethyl-3-(6-n-propyl-8$\alpha$-ergolinyl)urea, 2.7 g of pulverized KOH, 217 mg of tetrabutylammonium hydrogen sulfate, and 5.5 ml of n-propyl iodide are stirred in 100 ml of absolute tetrahydrofuran for 5 hours at room temperature. After adding 50 ml of $H_2O$, the mixture is extracted with ethyl acetate, rinsed, and dried, thus obtaining 1.8 g (80% of theory) as an oil $[\alpha]_D = +2.6°$ (c=0.5 $CHCl_3$)

1,1-Dioethyl-3-(1-ethyl-9,10-didehydro-6-methyl-8$\alpha$-ergolinyl)urea is produced analogously to the above procedure from lisuride by $N^1$-alkylation with ethyl iodide in the presence of KOH and tetrabutylammonium hydrogen sulfate in quantitative yield.

EXAMPLE 1

1,1-Diethyl-3-(6-methyl-8$\alpha$-ergolinyl)thiourea (a) A solution of 1.4 g of phosphorus oxychloride in 10 ml of absolute dichloromethane is cooled to $-20°$ C. and combined under nitrogen with 1.0 g of 1,1-diethyl-3-(6-methyl-8$\alpha$-ergolinyl)urea. The reaction mixture is stirred for 6 hours at $-20°$ C., then overnight at room temperature. After removing dichloromethane and excess $POCl_3$ by distillation (under vacuum), the residue is mixed under agitation and with exclusion of moisture with diethyl ether, and the crystalline mixture is quickly suctioned off and dried over $P_2O_5$.

The hygroscopic crystallized product is suspended in 10 ml of absolute acetonitrile, cooled to $-10°$ C., and combined with 1.5 g of potassium ethylxanthate. After agitation of the suspension overnight under nitrogen and exclusion of moisture at room temperature, the acetonitrile is removed by distillation, the residue is stirred together with $NaHCO_3$ solution and ethyl acetate, the organic phase is separated and concentrated under vacuum. The residue is crystallized from dichloromethane/diisopropyl ether, yielding 0.9 g (84.2%) of thiourea, mp 205°–207° C. $[\alpha]_D = +38°$ (c=0.5, CHCl$_3$)

(b) The activated urea derivative prepared according to Example 1(a) is reacted with potassium ethylxanthate in dimethylformamide under analogous conditions to the thiourea. Yield: 81%, mp 206° C.

(c) The activated urea derivative produced in accordance with Example 1(a) is reacted with sodium sulfide in acetonitrile to the thiourea. Yield: 76%, mp 207° C.

(d) The activated urea derivative prepared according to Example 1(a) is stirred with potassium ethylxanthate in ethanol (absolute) at −20° C. for 30 minutes, then maintained for 2 hours at room temperature. Subsequently, under ice cooling, the mixture is combined dropwise with 4N KOH and precipitated with water. Yield: 81.9%.

The following compopunds are prepared analogously to 1(a):

| 1,1-Diethyl-3-(9,10-didehydro-6-methyl-8α-ergolinyl)-thiourea |
|---|
| $[\alpha]_D = +395°$ (c = 0.5, pyridine), from 1,1-diethyl-3-(9,10-didehydro-6-methyl-8α-ergolinyl)urea. |
| 3-(2-Bromo-6-methyl-8α-ergolinyl)-1,1-diethylthiourea |
| $[\alpha]_D = +46°$ (c = 0.5, MeOH), from 3-(2-bromo-6-methyl-8α-ergolinyl)-1,1-diethylurea. |
| 1,1-Diethyl-3-(1-ethyl-9,10-didehydro-6-methyl-8α-ergolinyl)thiourea |
| $[\alpha]_D = +354°$ (c = 0.5, CHCl$_3$), from 1,1-diethyl-3-(1-ethyl-9,10-didehydro-6-methyl-8α-ergolinyl)urea. |

EXAMPLE 2

1,1-Diethyl-3-(2-iodo-6-methyl-8α-ergolinyl)thiourea

A solution of 0.17 g of phosphorus oxychloride in 8 ml of dichloromethane, cooled to −20° C., is combined under a nitrogen atmosphere with 0.17 g of 1,1-diethyl-3-(2-iodo-6-methyl-8α-ergolinyl)urea and stirred at this temperature for 5 hours, then overnight at room temperature. After the solvent has been removed by distillation, the residue is stirred into diethyl ether and the solvent again distilled off under vacuum. The dry residue is combined, without isolation, with 5 ml of acetonitrile (absolute) and stirred, while cooling to −10° C., with 0.18 g of potassium ethylxanthate for 4 hours under nitrogen, then overnight at room temperature. After the mixture has been worked up—as in Example 1—the crude product is purified over silica gel with deichloromethane and crystallized from pentane/diethyl ether. Yield: 116 mg (64%), mp 198° C.; $[\alpha]_D = +59°$ (c=0.5, CHCl$_3$)

The following thioureas are prepared analogously:

| 3-(2-Bromo-9,10-didehydro-6-methyl-8α-ergolinyl)-1,1-diethylthiourea |
|---|
| $[\alpha]_D = +385.2°$ (c = 0.5, pyridine), from 3-(2-bromo-9,10-didehydro-6-methyl-8α-ergolinyl)-1,1-diethylurea. |
| 1,1-Diethyl-3-(1,6-di-n-propyl-8α-ergolinyl)thiourea |
| $[\alpha]_D = +39.4°$ (c = 0.5, CHCl$_3$), from 1,1-diethyl-3-(1,6-di-n-propyl-8α-ergolinyl)urea. |
| 1,1-Diethyl-3-(1-ethyl-6-methyl-8α-ergolinyl)thiourea |
| $[\alpha]_D = +28°$ (c = 0.5, CHCl$_3$), from 1,1-diethyl-3-(1-ethyl-6-methyl-8α-ergolinyl)urea. |
| 1,1-Diethyl-3-(6-methyl-2-methylthio-8α-ergolinyl)thiourea |
| $[\alpha]_D = +55°$ (c = 0.5, CHCl$_3$), from 1,1-diethyl-3-(6-methyl-2-methylthio-8α-ergolinyl)urea. |

| 1,1-Diethyl-3-(6-methyl-8α-ergolinylmethyl)thiourea |
|---|
| $[\alpha]_D = -28°$ (c = 0.5, pyridine), from 1,1-diethyl-3-(6-methyl-8α-ergolinylmethyl)urea. |
| 3-(9,10-Didehydro-6-methyl-8α-ergolinylmethyl)-1,1-diethylthiourea |
| $[\alpha]_D = +264°$ (c = 0.5, pyridine), from 3-(9,10-didehydro-6-methyl-8α-ergolinylmethyl)urea. |
| 1-(9,10-Didehydro-6-methyl-8α-ergolinyl)thiourea |
| $[\alpha]_D = +398°$ (c = 0.25, pyridine), from 1-(9,10-didehydro-6-methyl-8α-ergolinyl)urea. |
| 3-(9,10-Didehydro-6-methyl-8β-ergolinyl)-1,1-diethylthiourea |
| $[\alpha]_D = +185°$ (c = 0.5, pyridine), from 3-(9,10-didehydro-6-methyl-8β-ergolinyl)-1,1-diethylurea. |
| 1-Ethyl-3-(9,10-didehydro-6-methyl-8α-ergolinyl)thiourea |
| $[\alpha]_D = +406°$ (c = 0.5, CHCl$_3$), from 1-ethyl-3-(9,10-didehydro-6-methyl-8α-ergolinyl)urea. |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for the preparation of ergolinylthiourea compounds of the formula

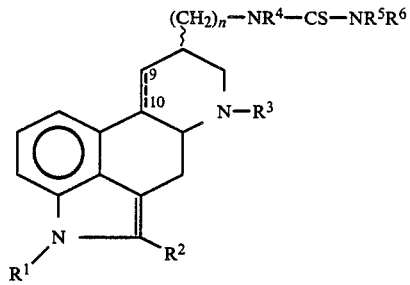

wherein
$R^1$ is hydrogen, lower alkyl or acyl derived from a carboxylic acid,
$R^2$ is hydrogen, halogen or lower alkylthio,
$R^3$ is lower alkyl,
$R^4$, $R^5$ and $R^6$ is hydrogen or lower alkyl,
n=0, 1 or 2 and
$C_9$—$C_{10}$ is a single or a double bond, which comprises reacting an argolin-8 -ylurea compound of the Formula

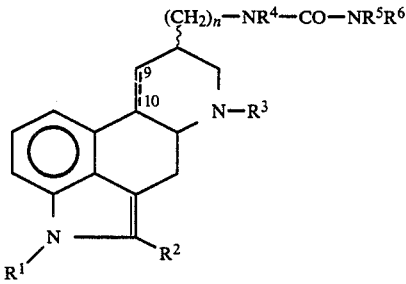

wherein $R^1$, $R^2$, $R^3$, $R^4$, $R^5$, $R^6$ and $C_9$—$C_{10}$ have the values given above, with phosphorous oxychloride and then with a thiolating agent that is an alkali metal xanthate, alkali metal or alkaline earth metal sulfide, thiourea or Bunte salt.

2. A process of claim 1, wherein the thiolating agent is an alkali metal xanthate.

3. A process of claim 2, wherein the thiolating agent is an alkali metal sulfide.

4. A process of claim 1, wherein the ergolin-8-ylurea compound is 1,1-diethyl-3-(1,6-di-n-propyl-8α-ergolinyl)urea.

5. A process of claim 1, wherein the ergolin-8-ylurea compound is 1,1-diethyl-3-(1-ethyl-9,10-didehydro-6-methyl-8α-ergolinyl) urea.

6. A process of claim 1, wherein the ergolin-8-ylurea compound is 3-(2-bromo-6-methyl-8α-ergolinyl)-1,1-diethylurea.

7. A process of claim 1, wherein the ergolin-8-ylurea compound is 1,1-diethyl-3-(1-ethyl-9,10-didehydro-6-methyl-8α-erglinyl)urea.

8. A process of claim 1, wherein the ergolin-8-ylurea compound is 1,1-diethyl-3-(2-iodo-6-methyl-8α-ergolinyl)urea.

9. A process of claim 1, wherein the ergolin-8-ylurea compound is 3-(2-bromo-9,10-didehydro-6-methyl-8α-ergolinyl)-1,1-diethylurea.

10. A process of claim 1, wherein the ergolin-8-ylurea compound is 1,1-diethyl-3-(1,6-di-n-propyl-8α-ergolinyl)urea.

11. A process of claim 1, wherein the ergolin-8-ylurea compound is 1,1-diethyl-3-(1-ethyl-6-methyl-8α-ergolinyl)urea.

12. A process of claim 1, wherein the ergolin-8-ylurea compound is 1,1-diethyl-3-(6-methyl-2-methylthio-8α-ergolinyl)urea.

13. A process of claim 1, wherein the ergolin-8-ylurea compound is 1,1-diethyl-3-(6-methyl-8α-ergolinylmethyl)urea.

14. A process of claim 1, wherein the ergolin-8-ylurea compound is 3-(9,10-didehydro-6-methyl-8α-ergolinylmethyl)urea.

15. A process of claim 1, wherein the ergolin-8-ylurea compound is 1-(9,10-didehydro-6-methyl-8α-ergolinyl)urea.

16. A process of claim 1, wherein the ergolin-8-ylurea compound is 3-(9,10-didehydro-6-methyl-8α-ergolinyl)-1,1-diethylurea.

17. A process of claim 1, wherein the ergolin-8-ylurea compound is 1-ethyl-3-(9,10-didehydro-6-methyl-8α-ergolinyl)urea.

* * * * *